(12) United States Patent
Oswald et al.

(10) Patent No.: US 12,048,654 B2
(45) Date of Patent: Jul. 30, 2024

(54) PATIENT POSITIONING DEVICE FOR AN X-RAY IMAGING APPARATUS

(71) Applicant: Siemens Healthcare GmbH, Erlangen (DE)

(72) Inventors: Johannes Oswald, Forchheim (DE); Gregor Niewalda, Buckenhof (DE); Michael Wiets, Langensendelbach (DE)

(73) Assignee: Siemens Healthineers AG, Forchheim (DE)

( * ) Notice: Subject to any disclaimer, the term of this patent is extended or adjusted under 35 U.S.C. 154(b) by 504 days.

(21) Appl. No.: 17/312,601

(22) PCT Filed: Oct. 24, 2019

(86) PCT No.: PCT/EP2019/078989
§ 371 (c)(1),
(2) Date: Jun. 10, 2021

(87) PCT Pub. No.: WO2020/119992
PCT Pub. Date: Jun. 18, 2020

(65) Prior Publication Data
US 2022/0039764 A1 Feb. 10, 2022

(30) Foreign Application Priority Data

Dec. 11, 2018 (DE) .......................... 10 2018 221 421

(51) Int. Cl.
*A61G 13/10* (2006.01)
*A61B 6/04* (2006.01)
(Continued)

(52) U.S. Cl.
CPC .......... *A61G 13/105* (2013.01); *A61B 6/0442* (2013.01); *A61G 13/0036* (2013.01);
(Continued)

(58) Field of Classification Search
CPC .. A61G 13/08; A61G 13/129; A61G 13/0036; A61G 13/105; A61G 2203/16;
(Continued)

(56) References Cited

U.S. PATENT DOCUMENTS 4,474,364 A * 10/1984 Brendgord ............. A61G 13/08
5/619
6,634,043 B2 * 10/2003 Lamb ................. A61G 13/0036
5/624
(Continued)

FOREIGN PATENT DOCUMENTS

CN     205094920 U     3/2016
CN     205198377 U     5/2016
(Continued)

OTHER PUBLICATIONS

German Office Action for German Application No. 10 2018 221 421.2 dated Sep. 27, 2019.
(Continued)

*Primary Examiner* — Justin C Mikowski
*Assistant Examiner* — Madison Emanski
(74) *Attorney, Agent, or Firm* — Lempia Summerfield Katz LLC

(57) ABSTRACT

The invention relates to a patient positioning device (1, 6, 28, 35) for an x-ray imaging apparatus (23), comprising an x-ray-transparent patient positioning board (5) for positioning a patient (21) in a longitudinal direction (8), and at least one carrier device (3) at least partially supporting the patient positioning board (5). The patient positioning board (5) is subdivided into at least two partial boards (4), wherein each partial board (4) is mounted on a carrier device (3) assigned to the partial board (4). Each carrier device (3) has at least one pivot joint for pivoting the partial boards (4) about a transverse axis (20) which extents horizontally perpendicularly to the longitudinal direction (8).

20 Claims, 9 Drawing Sheets

(51) Int. Cl.
*A61G 13/00* (2006.01)
*A61G 13/04* (2006.01)
*A61G 13/08* (2006.01)

(52) U.S. Cl.
CPC .......... *A61G 13/0054* (2016.11); *A61G 13/04* (2013.01); *A61G 13/08* (2013.01); *A61G 2203/16* (2013.01); *A61G 2210/50* (2013.01)

(58) Field of Classification Search
CPC .... A61G 7/015; A61G 13/04; A61G 13/0054; A61G 7/018; A61G 13/06; A61G 13/123; A61G 7/005; A61G 7/012; A61G 13/1245; A61G 2210/50; A61G 13/02; A61G 13/121; A61B 6/4405; A61B 6/0442; A61B 6/04; A61B 6/0407; A47C 20/041; A47C 19/045; A47C 20/08
USPC ...................................... 5/613, 942; 378/209
See application file for complete search history.

(56) References Cited

U.S. PATENT DOCUMENTS

| 7,730,565 B1 * | 6/2010 | Masson .................... A61G 1/04 5/503.1 |
| 7,913,337 B1 * | 3/2011 | Masson ................ A61G 1/0212 5/942 |
| 2004/0133979 A1 | 7/2004 | Newkirk |
| 2006/0185090 A1 | 8/2006 | Jackson |
| 2007/0238949 A1 * | 10/2007 | Wang .................... A61B 6/0478 600/407 |
| 2008/0262657 A1 * | 10/2008 | Howell ................ A47C 20/041 700/275 |
| 2013/0133137 A1 | 5/2013 | Jackson et al. |
| 2016/0000621 A1 * | 1/2016 | Jackson ............... A61G 13/122 5/618 |
| 2018/0221230 A1 * | 8/2018 | Smith ....................... A61F 5/04 |

FOREIGN PATENT DOCUMENTS

| CN | 106361527 A | | 2/2017 | |
| CN | 206934288 U | | 1/2018 | |
| CN | 109393815 | * | 9/2019 | ............. A61G 13/08 |
| DE | 102011108347 A1 | | 1/2013 | |
| DE | 102013215454 A1 | | 2/2015 | |
| DE | 102019203882 B3 | * | 3/2019 | ............... A61B 6/04 |
| EP | 2674143 A2 | | 12/2013 | |
| WO | WO-2016197142 A1 | * | 12/2016 | ......... A61G 13/0081 |

OTHER PUBLICATIONS

International Search Report and the Written Opinion for International Patent Application PCT/EP2019/078989 mailed Feb. 25, 2020.

* cited by examiner

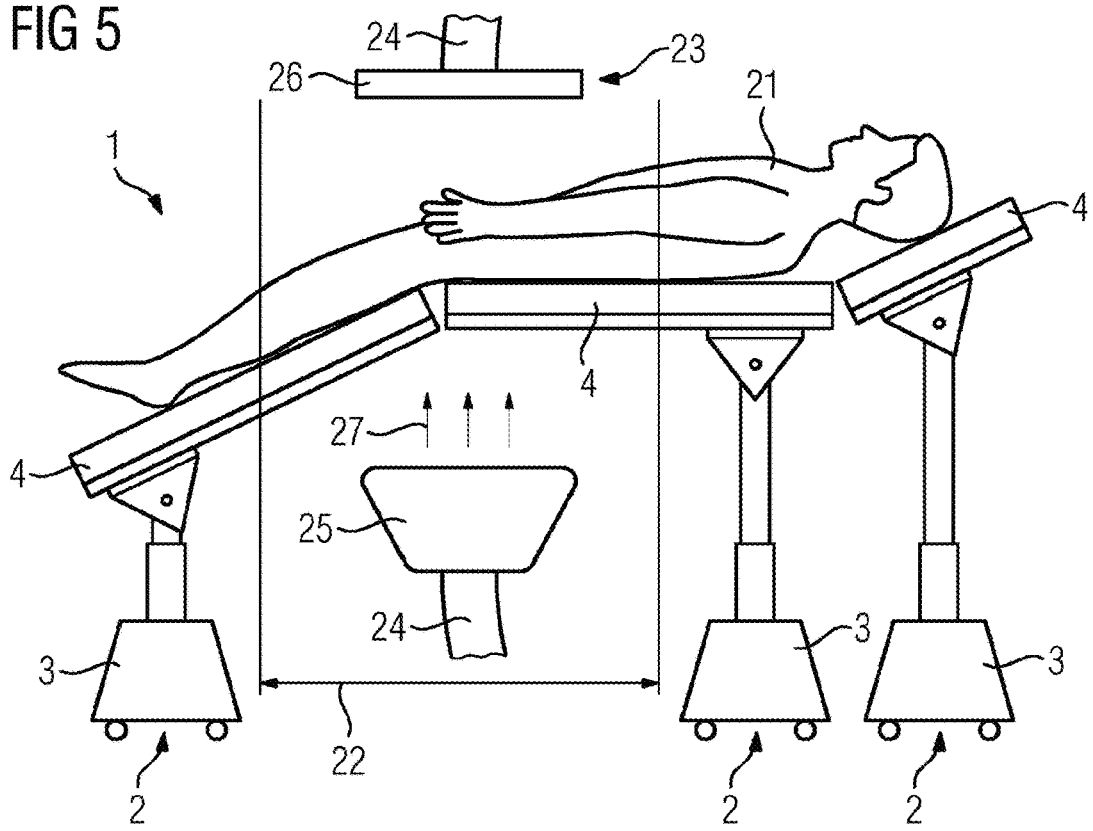
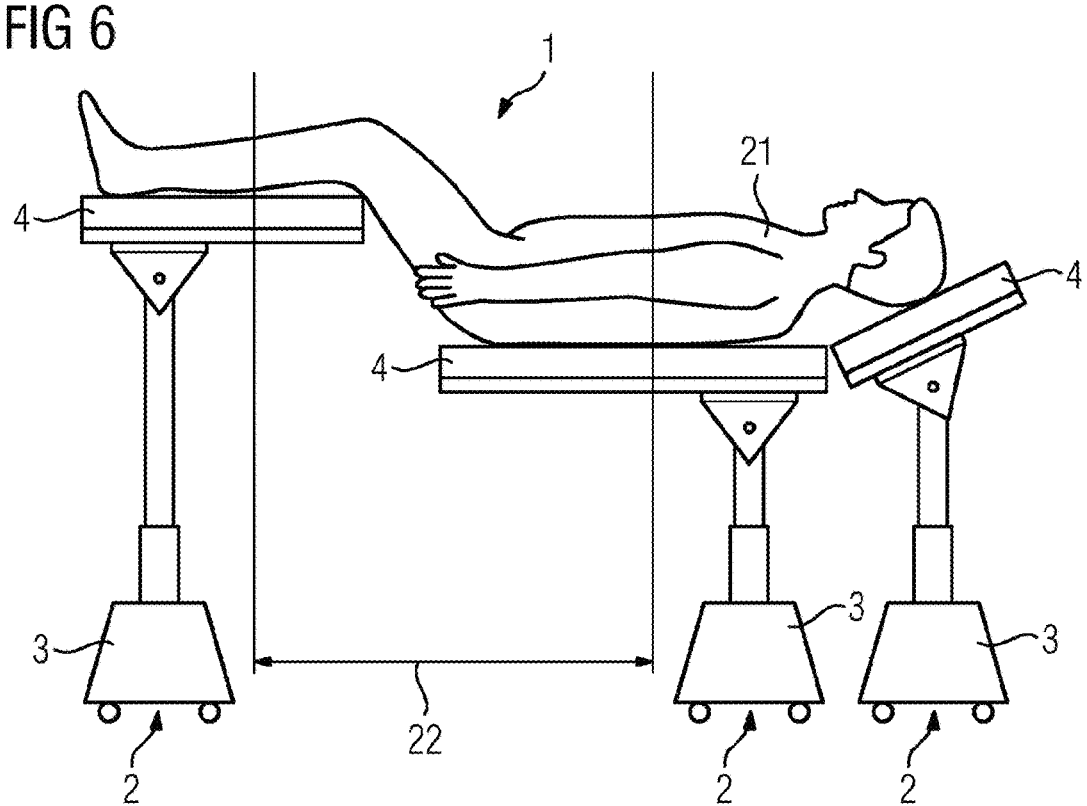

PATIENT POSITIONING DEVICE FOR AN X-RAY IMAGING APPARATUS

CROSS REFERENCE TO RELATED APPLICATIONS

This present patent document is a § 371 nationalization of PCT Application Serial Number PCT/EP2019/078989 filed on Oct. 24, 2019, designating the United States, which is hereby incorporated in its entirety by reference. This patent document also claims the benefit of DE 102018221421.2 filed on Dec. 11, 2018 which is hereby incorporated in its entirety by reference.

FIELD

Embodiments relates to a patient positioning device for an x-ray imaging device including an x-ray-transparent patient positioning board for positioning a patient in a longitudinal direction and at least one carrier device at least partially supporting the patient positioning board.

BACKGROUND

Patient positioning devices that may be configured in various ways are important tools in the context of surgical interventions on patients. The possibility of intraoperative imaging during such surgical interventions is also increasingly important, and therefore patient positioning devices are already proposed in which at least the patient positioning board is x-ray-transparent, meaning that it attenuates the x-radiation so little that diagnostically relevant x-ray imaging through the patient positioning board is also possible.

It is however problematic in this context that many surgical interventions require specific arrangements of the patient supported on the patient positioning board. In the case of spinal surgery, for example, the patient is typically lying on their stomach during the operation. Operating tables such as the so-called Jackson table, for example, are used as patient positioning devices in this case. Using such a patient positioning device, the patient positioning board may be "raised" at the center in order that various patient positions may be set, for example bending at the middle of the body. However, such an operating table includes a linkage below the patient positioning board, that makes radioscopy extremely difficult. The stiffening elements are moreover made of metal, that also impedes and may completely prevent the radioscopy. This is attributable to the fact that metals in the beam path result in distinct artifacts that may in some cases render the subject unrecognizable.

In addition to the cited example of bending at the middle of the body, other requirements also exist in the context of operations, and therefore operating tables have been proposed as patient positioning devices in which partial boards may be pivoted relative to each other at more than one midpoint. For example, individual partial boards for both legs are proposed in order to achieve the so-called "lithotomy position". Although x-ray-transparent joints for operating tables are already proposed in the prior art, existing operating tables offering multiple folding and adjustment options are not sufficiently or fully x-ray-transparent for the intended applications.

BRIEF SUMMARY AND DESCRIPTION

The scope of the embodiments is defined solely by the appended claims and is not affected to any degree by the statements within this summary. The present embodiments may obviate one or more of the drawbacks or limitations in the related art.

Embodiments provide a patient positioning device as an operating table for surgical interventions, offering excellent transparency characteristics for x-ray imaging at least in an operating region.

In a patient positioning device, for example an operating table, the patient positioning board may be divided into at least two partial boards. Each partial board is mounted on a carrier device assigned to the partial board, and for each carrier device to have at least one pivot joint for pivoting the partial boards about a transverse axis that extends horizontally and perpendicularly to the longitudinal direction.

The carrier devices may be support columns for example. Since it is customary in the case of existing patient positioning devices, for example operating tables, to use a single carrier device, for example a single support column, the embodiments described herein not only divide the patient positioning board into partial boards, but also assign to each of these partial boards a dedicated carrier device on which the corresponding partial board is so mounted as to be at least pivotable about a transverse axis that extends in a transverse direction. Each carrier device includes at least one height adjustment device for height adjustment of the respective partial board and/or one longitudinal adjustment device for longitudinal displacement of the respective partial board. Further degrees of freedom/adjustment devices are also possible, including further pivot joints if applicable. In order to simplify the description of the patient positioning device, the height adjustment devices and/or longitudinal adjustment devices are both designated as "adjustment devices" in the following.

Carrier devices with their respective partial boards may be considered as a type of module of the patient positioning device, for example the operating table. The combination of at least two modules, in many cases at least three modules provides the desired function of a fully featured operating table where each module may be deployed in a flexible manner. By positioning and setting of the individual modules, using the pivot joint and optionally the adjustment devices, it is possible to realize a variety of common operating positions. It was recognized in this context that the operating region or region of surgical intervention is usually located at the region in which partial boards that may be adjusted relative to each other meet. With the exception of the partial boards (and any connections), specifically this region is kept clear, i.e., clear of pivot joints, adjustment devices and carrier devices, such that high-quality x-ray imaging may be achieved there by virtue of the x-ray-transparent embodiment of the patient positioning board.

As mentioned above and explained in greater detail below, by combining different carrier devices with partial boards, it is possible using the patient positioning device to create operating tables that may be variably set in different ways. Specific patient positions are possible for urology, orthopedics and gynecology, including for example, the so-called lithotomy position. In the specific case of the lithotomy position, two modules may function as leg holders with the advantage that an x-ray-transparent region of the patient positioning device is possible from the knee joint to the chest region, for example intraoperatively, without requiring a change of the patient position. By providing at least one longitudinal adjustment device it is also possible for example to achieve uniform and coordinated movement of the partial boards and thus the whole patient positioning board, and therefore the positioning of the patient is preserved while at the same time a region to be scanned may be repositioned in such a way that interfering carrier devices are no longer situated in the region of the x-ray scan performed by the x-ray imaging device.

In other words, the previous central carrier device, for example a support column, of a conventional operating table is divided into at least two carrier devices, for example support columns, so that suitable positioning of the carrier devices may be affected in such a way that x-ray imaging in relevant regions is not impeded by the carrier device. In an embodiment the carrier devices are arranged at the outside in a longitudinal direction, such that a larger area free of carrier devices is present at the middle of the patient positioning device for example.

In an embodiment, each carrier device, for example at least a foot of the carrier device, is configured such that even at both end positions of longitudinal adjustment the center of gravity remains above the footprint of the carrier device. Massive here signifies that shape, dimensions and mass are correspondingly selected. For example, in the case of a large contact area of the foot on the floor or in the case of more widely disposed contact points, a lower mass is sufficient for the center of gravity to remain above the footprint of the carrier device. Therefore, the carrier devices, for example modules thereof, may also be configured in a stable manner such that their function of supporting the partial board is guaranteed at every permitted horizontal displacement setting, for example longitudinal displacement setting. It is possible in this case to exploit the fact that the carrier devices, for example the feet thereof, need not include x-ray-transparent material and may therefore be configured in a correspondingly massive manner in order to provide adequate stability for all desired horizontal displacements of the partial board. Different carrier devices may also be provided for different points of use, for example, less massively dimensioned carrier devices for carrying extremities, and more massively dimensioned carrier devices for carrying a trunk or body. As a result of using less massively dimensioned carrier devices in regions of the patient positioning device where these are sufficient, it is possible to increase freedom of movement in these regions.

The height adjustment device of each carrier device, the carrier device being configured as a support column for example, may be configured as a telescopic device and/or the longitudinal adjustment device may include at least one guide rail. A telescopic device here is understood to mean that an inner carrier part is displaceably mounted in an outer carrier part such that the height of the carrier device may be changed by moving the inner carrier part out from the outer carrier part.

Where the carrier devices are configured as support columns, a cylindrical foot may be provided in which a vertically adjustable telescopic column (as a second carrier part) is displaceably mounted. The rotatably mounted pivot joint, i.e., an articulated apparatus that is mounted rotatably for example, may be attached to an upper end of the displaceable telescopic column. In an embodiment, a longitudinally displaceable rail may be fastened to the pivot joint, and the partial board attached to the rail. The guide rail may be configured in the form of a trapezoidal connecting member, for example, other embodiments may be possible.

Each pivot joint and/or each adjustment device is assigned a triggerable actuator for the respective adjustment thereof, the patient positioning device additionally including a control device for the purpose of triggering all actuators. A triggerable actuator system is therefore provided, for example for all adjustment possibilities, so that specific adjustments of the pivot joints and/or adjustment devices and thus the partial boards may be affected by a control device, for example, on the basis of operator inputs and/or stored presettings, for example in order that predefined patient positions suitable for surgical interventions may be produced. The pivot joint may not only be actively controllable, but also the longitudinal displacement of the partial board, for example on the guide rail, and the height adjustment, for example using a telescopic device. The control device may trigger a plurality of carrier devices and/or modules for example, such that in a coordinated manner all triggered carrier devices or modules form a patient positioning device whose height, shape and position are predefined by the control device.

The actuators may be realized in different ways, for example, by a cable control and/or a pinion in combination with a toothed rack and/or a chain and/or including a motor or similar. Corresponding technical devices are already known for the actuators of the pivot joints likewise.

The adjustment devices and/or pivot joints and/or actuators may be at least partially x-ray-transparent, for example with regard to components that could project into a possible x-ray imaging region. For example, guide rails, pinions and/or toothed racks may be manufactured from x-ray-transparent material, for example carbon-fiber materials and/or carbon-fiber composite materials.

According to an embodiment, the control device is configured to compensate at least partially for a separation between the partial boards, caused by pivoting of the partial boards, by longitudinal displacement and/or height adjustment of the partial boards. For this purpose, the control device may include an intelligence that is realized by hardware and/or software and that, for example following corresponding selection by an operator, provides that the partial boards continue to form a contiguous patient positioning board. For reasons of stability and materials it is appropriate in this context for the partial boards to be so configured as to be of sufficient length and for any extensibility or similar to be excluded.

Therefore, if a case is presented in which the patient positioning board is divided centrally into two partial boards and attached to the two carrier devices via a corresponding pivot joint, and it is required to produce bending of the patient at the middle of the body, the two partial boards may be rotated via the pivot joints, possibly synchronously. In this case, the partial boards separate in the middle, and this may be compensated by a simultaneous sliding movement of the two partial boards towards each other.

Other coordinated movements may also be affected by the control device or a corresponding processor thereof.

The control device may be configured to receive signals from an operating device that is assigned to the patient positioning device at least at certain times. In this case, the operating device may also be part of the patient positioning device. In addition to the use of "conventional" operating devices, for example an operating device with mechanical operating elements, for example including switches, buttons and similar, an embodiment provides for the operating device to be a mobile device, for example a tablet, having a touch screen for displaying a manipulatable representation of the patient positioning device. In this case, the manipulatable representation includes at least a display of the current positions and arrangements of the partial boards. For example, by specific gestures performed in relation to the displayed partial boards, their position and arrangement (orientation) may initially be changed within the manipulatable representation. While this might immediately result in the actuators being triggered in order to correct the actual position and arrangement, it is also possible by manipulating all partial boards or other represented components of the patient positioning device to first define a desired overall setting that may then be selected via a specific operating element, for example an operating element that also belongs to the touch screen. Following selection via the corresponding operating element, the actuators are then triggered by the control device in order to realize the overall setting. It is moreover also possible to provide a plurality of operating modes on the operating device, for example, a direct operating mode and an overall setting operating mode, or even coordination operating modes for coordinated movement of the partial boards as described above. Further embodiments provided by modern touch screens are also possible, for example, the selection of individual modules including carrier device and partial board for the purpose of discrete operation and similar. Furthermore, embodiments are also possible in which the touch screen is assigned to an operating device that is permanently assigned to the patient positioning device. If the operating device is configured as a mobile device, the operating functionality via the touch screen may be provided via a software application ("app") for example.

The connection of the control device to the operating device may be established wirelessly, for example using conventional wireless technologies for example, Bluetooth and/or WLAN may be deployed for this purpose.

Basic arrangements assigned to different types of operation, i.e., types of surgical intervention, may be stored in the control device and then implemented when the corresponding basic arrangement is selected by a user. Basic arrangements are overall settings that are assigned to specific types of surgical interventions. Once such a basic arrangement has been selected and implemented, it is possible via the operating device for example, that may appropriately be used to also select the basic arrangement, to make fine adjustments for the patient concerned. An automatic selection of a basic arrangement or a suggestion for a basic arrangement may also be output by the control device, for example, if the control device is connected to an information system, for example, a hospital information system (HIS) and/or a radiology information system (RIS), from which it is possible automatically to determine which type of surgical intervention is to be performed on which patient.

In an embodiment, in the case of partial boards which abut each other in a plane, for example a horizontal plane, the control device may be configured to trigger the adjustment devices in a coordinated manner in order to achieve overall movement of the complete patient positioning board. For example, if a patient is to be examined without specific bending, for example, in a horizontal position, it is possible to proceed in a conventional manner using such an embodiment of the patient positioning device. For example, overall movement of the complete patient positioning board may be performed horizontally and/or vertically. This requires the synchronization, provided by the control device, of the two partial boards or of the corresponding adjustment devices. It is also possible in this context to link the partial boards mechanically, whereby a narrow slot that might be present between partial boards may also be covered over.

The patient positioning device, even when configured as an operating table, may be used appropriately for examining a patient without surgical intervention, for example if specific arrangements are already desirable for the examination or if it is required to scan examination regions at locations where a carrier device might be situated in the case of conventional patient tables.

The pivot joints, that include x-ray-opaque material for example, may be arranged at the outside in a longitudinal direction, in or on the carrier device. For example, if the pivot joints include x-ray-opaque material and should not be "in the way" of x-ray imaging, it is appropriate to move these as far out as possible, on or in the carrier device, so that the central x-ray imaging region that is ideally free of x-ray-opaque material remains as large as possible.

At least two of the at least two adjacent partial boards may be connected to each other on their facing sides by a x-ray-transparent connection that is for example detachable and/or flexible and/or stretchable. In this case, a very wide range of embodiments are possible and may be deployed in accordance with the main application fields of the patient positioning device. It is therefore possible, for example, to provide detachable a connection between adjoining partial boards. For example, it is possible by a detachable connection to produce a secure mechanical coupling, for example, in the case of a desired secure arrangement of the partial boards relative to each other, for example in the case of partial boards that, resembling a conventional patient positioning board, are horizontally aligned and abut each other in a plane as described above. If pivoting of the partial boards relative to each other is required, the detachable connection may then be removed and the corresponding pivot adjustment may take place. A flexible and/or stretchable coupling of the partial boards relative to each other may also have advantages if a corresponding flexible and/or stretchable connection is provided. Such a flexible and/or stretchable connection between partial boards may even be left on the respective partial boards when the partial boards are pivoted relative to each other and/or if the partial boards are otherwise at least slightly separated from each other. Any slot that occurs is automatically covered over so that pinching of the patient is avoided.

An embodiment is provided in which a secure and/or flexible/stretchable coupling is established by the connection when required, for example if the partial boards come closer together than a lower threshold value for the separation. For example, the connection in such a case may have magnetic connectors that may, for example by a corresponding surface profiling/guide structure, interconnect in a defined manner and establish the coupling. The magnetic connectors may be fastened to the sides of the partial boards for example, by elastic fasteners, for example by springs or similar. An articulated body that is for example, cylindrical and/or spherical and is for example disposed centrally may be provided to allow defined movement of the magnetic connectors relative to the sides of the partial boards.

In an embodiment, for at least two of the at least two adjacent partial boards, at least one of the facing surfaces of the partial boards and/or connections may include at least one guide projection that engages into a corresponding guide recess of the other surface and allows an angular arrangement of the partial boards relative to each other when engaged. Partial boards of a module may be so configured in a longitudinal direction that a first partial board may be effectively supported by a partial board of an adjacent module, in order to achieve greater static certainty and therefore also greater stability. The connection of the partial boards may be realized for example by a reciprocal design of bulges and cavities. In this context, the at least one guide projection is partially spherical or partially cylindrical. As a result of the spherical or circular geometry, the partial boards may be brought together in any angle of incidence and at the same time prevented from slipping against each other. At least one of the surfaces perpendicular to the longitudinal direction and to the transverse direction, and adjacent to the guide projection and/or the guide recess, may be so configured as to recede and/or to allow room for the partial boards to tilt relative to each other.

The patient positioning board may be divided centrally into two partial boards. It is possible to produce a functionally identical replacement for the patient positioning devices, for example operating tables, based on the Jackson principle as cited in the background.

In certain embodiments to the use of two modules and one central division of the patient positioning board, the patient positioning device may include at least three partial boards and/or for at least two partial boards that are adjacently disposed in a transverse direction, and each assigned to a leg. Embodiments makes it possible to achieve the so-called lithotomy position. A swivel joint may be provided that allows pivoting about a vertical axis, at least for the partial boards that are each assigned to a leg.

All of the carrier devices or groups of the carrier devices may be structurally identical. Structurally identical carrier devices may be provided for both a high load capacity and mechanical stress and a low load capacity and mechanical stress respectively. A type of building block principle is realized, in which partial boards of different design, for example, different lengths and/or widths, may be attached to carrier devices, whereby different configurations of modules and therefore different patient positioning devices may be constructed using the same pool of resources. This includes advantages in terms of manufacturing and variability of the patient positioning devices.

The carrier devices may be at least partially mobile, including wheels for example. This not only facilitates the positioning of the patient positioning device in the room, but also allows different modules to be assembled in a flexible manner to form various specific patient positioning devices. Such wheels may also be assigned actuators, for example, motors, that may be triggered by the control device.

The patient positioning device, for example the patient table, may be assigned to a specific x-ray imaging device or form part of an x-ray imaging device. The x-ray-imaging device may be an x-ray device including a C-arm on which an x-ray source and an x-ray detector are arranged opposite each other. X-ray devices featuring such C-arms include an advantage that a very wide variety of suitable scanning geometries may be selected and it is also possible using the C-arm to extend at least partially under a gap between carrier devices, for example, and make optimum use of the x-ray imaging region that is provided by the special design of the patient positioning device. The control device of the x-ray device may also be configured for example to trigger actuators of the patient positioning device and therefore serve as a control device for the patient positioning device. Moreover, as described above, an operating device of the x-ray imaging device may also be designated for operation of the patient positioning device.

BRIEF DESCRIPTION OF THE FIGURES

FIG. 5 depicts a first possible overall setting according to an embodiment.

FIG. 6 depicts a second possible overall setting according to an embodiment.

DETAILED DESCRIPTION

Figure 1:
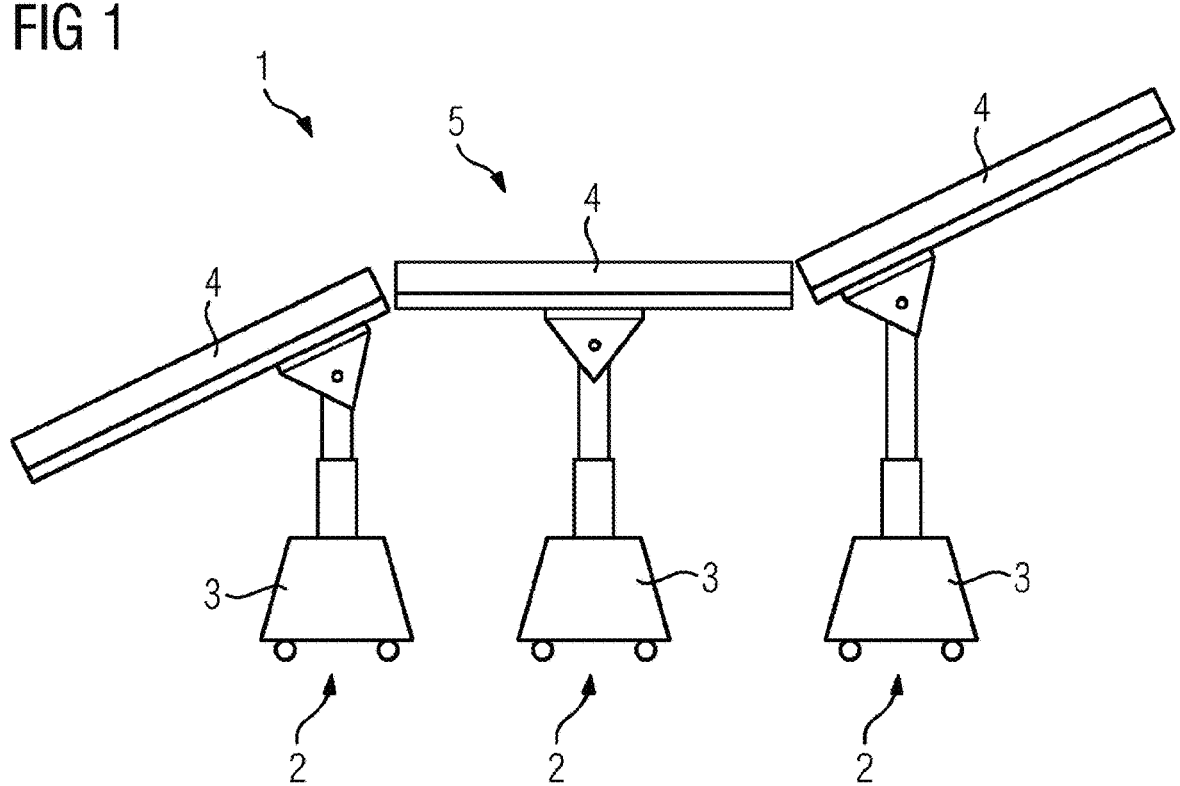
FIG. 1 depicts an embodiment of a patient positioning device including three modules.

FIG. 1 depicts a schematic view of an embodiment of a patient positioning device 1, including three modules 2, each of which includes a carrier device 3, for example a support column, and a partial board 4. The partial boards 4 together form a patient positioning board 5. At least the carrier devices are all structurally identical.

Figure 2:
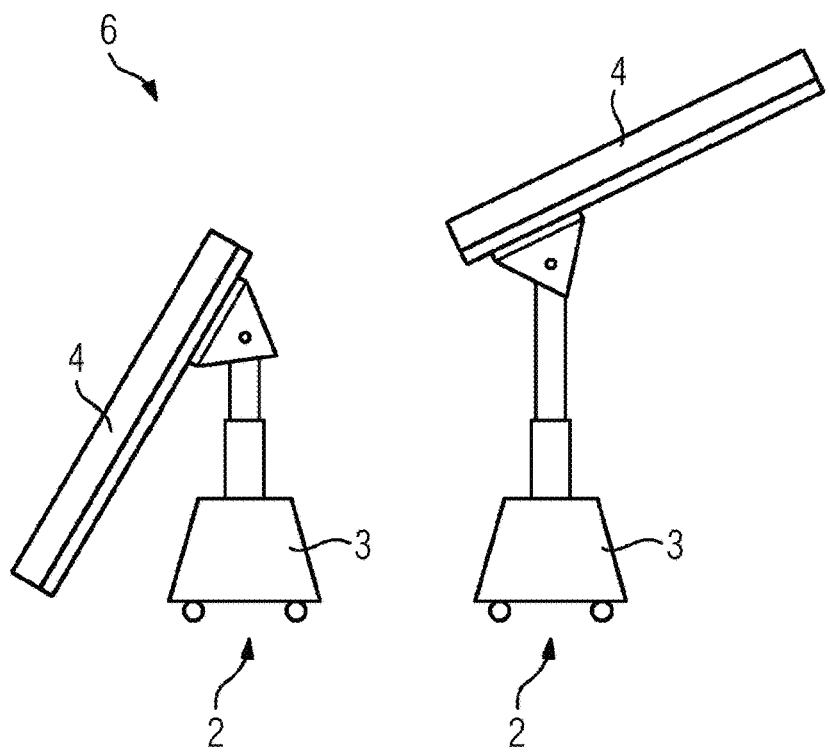
FIG. 2 depicts an embodiment of a patient positioning device, including two modules.

FIG. 2 depicts a second embodiment of a patient positioning device 6, including only two modules 2, the partial boards 4 of which have the same size, such that this may therefore be considered as a patient positioning board 5 that is centrally divided. As a result of the structurally identical carrier devices, both (and further) embodiments may be created from the same pool of resources.

Figure 3:
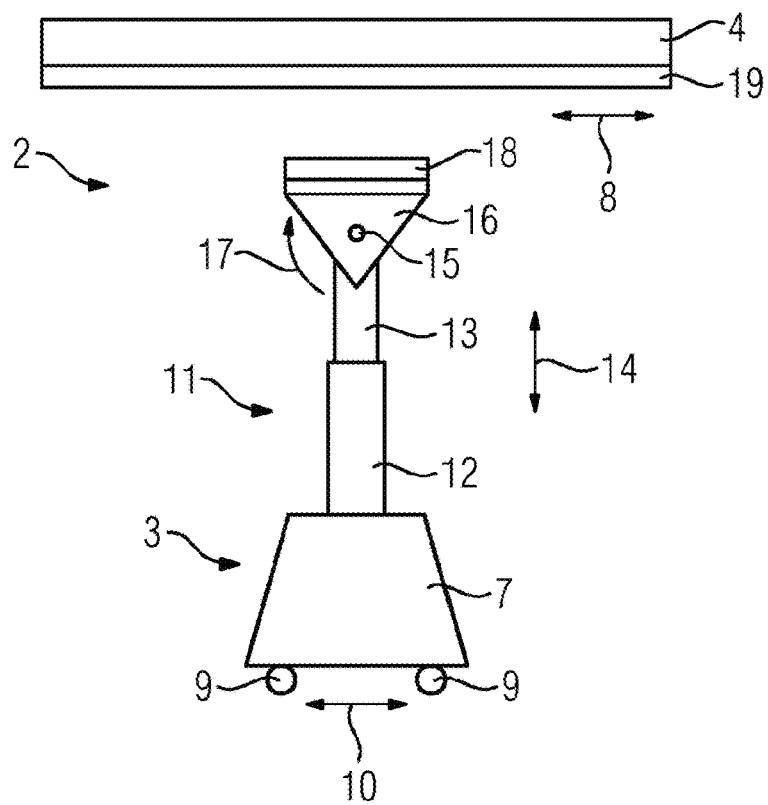
FIG. 3 depicts a side view of a module of a patient positioning device according to an embodiment.

FIG. 3 depicts the structure of the modules 2 in greater detail. The carrier devices 4, configured as support columns, for all partial boards 4 of all embodiments are configured identically in this case, meaning that any desired partial board 4 may be mounted on a carrier device 3 in order to create various types of patient positioning device. In this case, the carrier devices 3 include a foot 7 that is so configured as to be sufficiently massive that even in the event of maximal longitudinal displacement in a longitudinal direction 8, the partial board 4 does not tilt the module 2. Wheels 9 that may be locked by corresponding locking apparatuses allow mobility of the module 2 as indicated by the arrow 10. The wheels 9 may be assigned an actuator, for example, including a drive motor, in order to allow automatic movement controlled by a control device as explained in greater detail below.

The foot 7 supports a telescopic device 11 including an outer telescopic column 12 (as a first carrier part) in which an inner telescopic column 13 (as a second carrier part) is so mounted as to be adjustable in a vertical direction 14. The adjustment in a horizontal direction 14, i.e., the height adjustment, is likewise affected by an actuator that is not shown in further detail here. The telescopic device 11 therefore acts as a height adjustment device.

A further element 16 is fastened to the inner telescopic column 13 via a pivot joint 15. As illustrated by the arrow 17, the pivot joint 15 allows pivoting about a transverse axis that is perpendicular to the horizontal direction 14 and the longitudinal direction 8, and that extends in a transverse direction perpendicular to the plane of the drawing. The pivot joint 15 may likewise be operated via a triggerable actuator.

Figure 4:
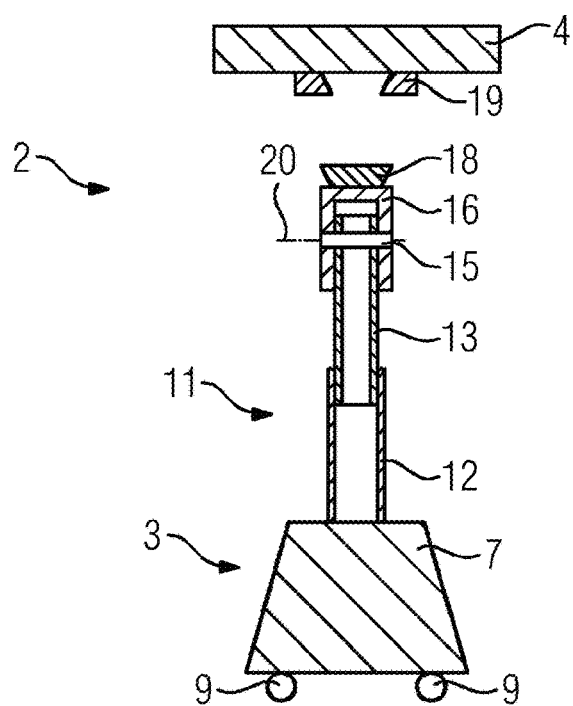
FIG. 4 depicts a cross-sectional view through the module from FIG. 3 according to an embodiment.

Arranged on the element 16 as part of a longitudinal adjustment device is a guide rail 18 that, as shown in FIG. 4, is trapezoidal in cross section and engages into a corresponding receiving rail 19 on the partial board 4. The longitudinal adjustment device thus formed also includes an assigned triggerable actuator that is not shown in further detail here. FIG. 4 also depicts the transverse axis 20 of the pivot joint 15.

Other embodiments may also feature further adjustment possibilities/actuators. The partial boards 4 are configured to be x-ray-transparent. At least parts of the carrier devices 3 may likewise be realized in an x-ray-transparent manner, for example by using carbon-fiber and/or glass-fiber composite materials (for example GRP, PEEK, etc.). Such materials may also be used for the partial boards 4 and further connections.

The actuators of the respective modules 2 are triggered by a shared control device, not shown in further detail here, to which an operating device may be assigned at least at certain times. The control device and the operating device may belong to the patient positioning device 1, 6 itself, but may also be realized as part of an x-ray imaging device that is configured to operate x-ray imaging during a surgical intervention. As set forth in greater detail below, use may be made of an operating device that includes a touch screen. The control device may also be used to store basic arrangements for various surgical interventions, which basic arrangements may be invoked by a user, whereupon the control device triggers the actuators in order to produce this basic arrangement.

Using the example of the patient positioning device 1, FIG. 5 depicts a first possible overall setting for a surgical intervention (or other examination of a patient 21) to be performed. In this case, the partial boards 4 of the outer modules 2 are visibly inclined by the pivot joints 15 while the central partial board 4 remains level. The carrier devices 3 of the central module 2 and of the left-hand module 2 in FIG. 6 have been moved outwards as far as possible in a longitudinal direction 8 by the longitudinal adjustment device and/or the wheels 9, thereby producing an extremely large x-ray imaging region 22 that may be used by an x-ray imaging device 23.

The x-ray imaging device 23 is an x-ray device featuring a C-arm 24, only partially indicated here, on which an x-ray source 25 and an x-ray detector 26 are arranged opposite each other. Since only the x-ray-transparent partial boards 4 are situated in the x-ray imaging region 22, the x-radiation indicated by the arrows 27 may penetrate these without difficulty and high-quality x-ray imaging is possible.

Figure 7:
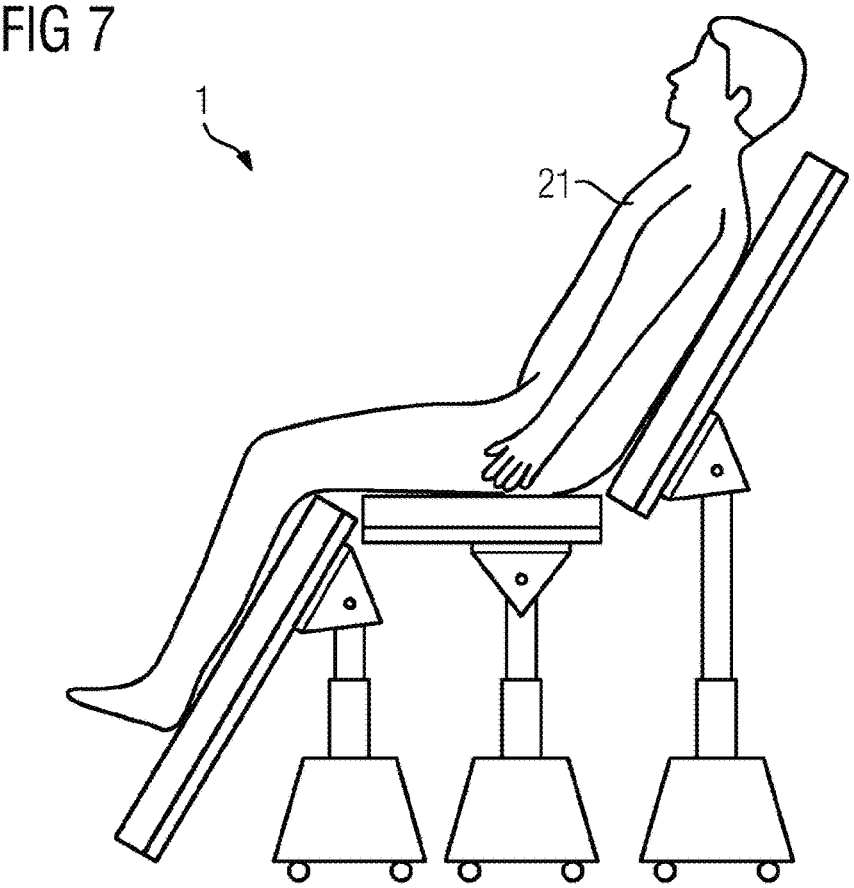
FIG. 7 depicts a third possible overall setting according to an embodiment.

FIGS. 6 and 7 depict further possibilities for overall settings of the patient positioning device 1. In FIGS. 6 and 7 the x-ray imaging regions 22 may be created at various positions in an extremely flexible manner.

Figure 8:
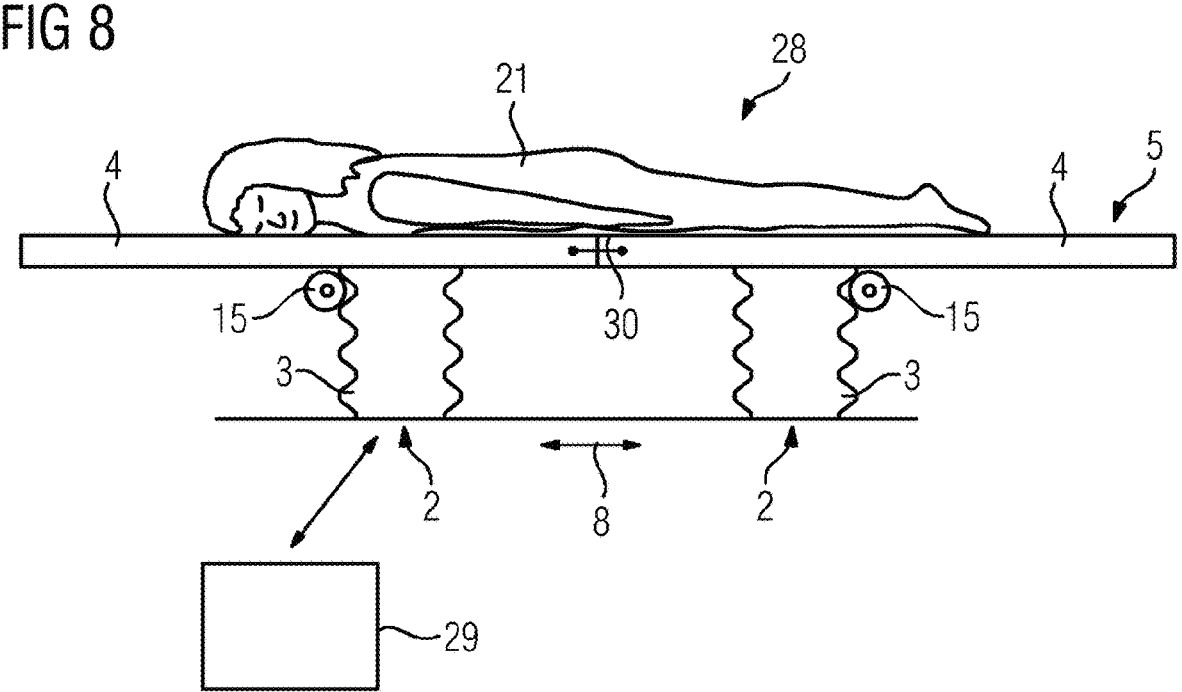
FIG. 8 depicts a schematic diagram of an embodiment of the patient positioning device in a first overall setting.

FIG. 8 depicts a schematic diagram of a further, third embodiment of a patient positioning device 28. This includes two fixed carrier devices 3 configured as support columns, on which the pivot joints 15 are visibly arranged on the outside in a longitudinal direction 8. The patient positioning board 5 is divided into two partial boards 4 that are equal in size but are longer, as shown in comparison with the patient 21. Furthermore, the control device 29 for controlling the respective actuators is also illustrated at least schematically in this diagram.

Figure 9:
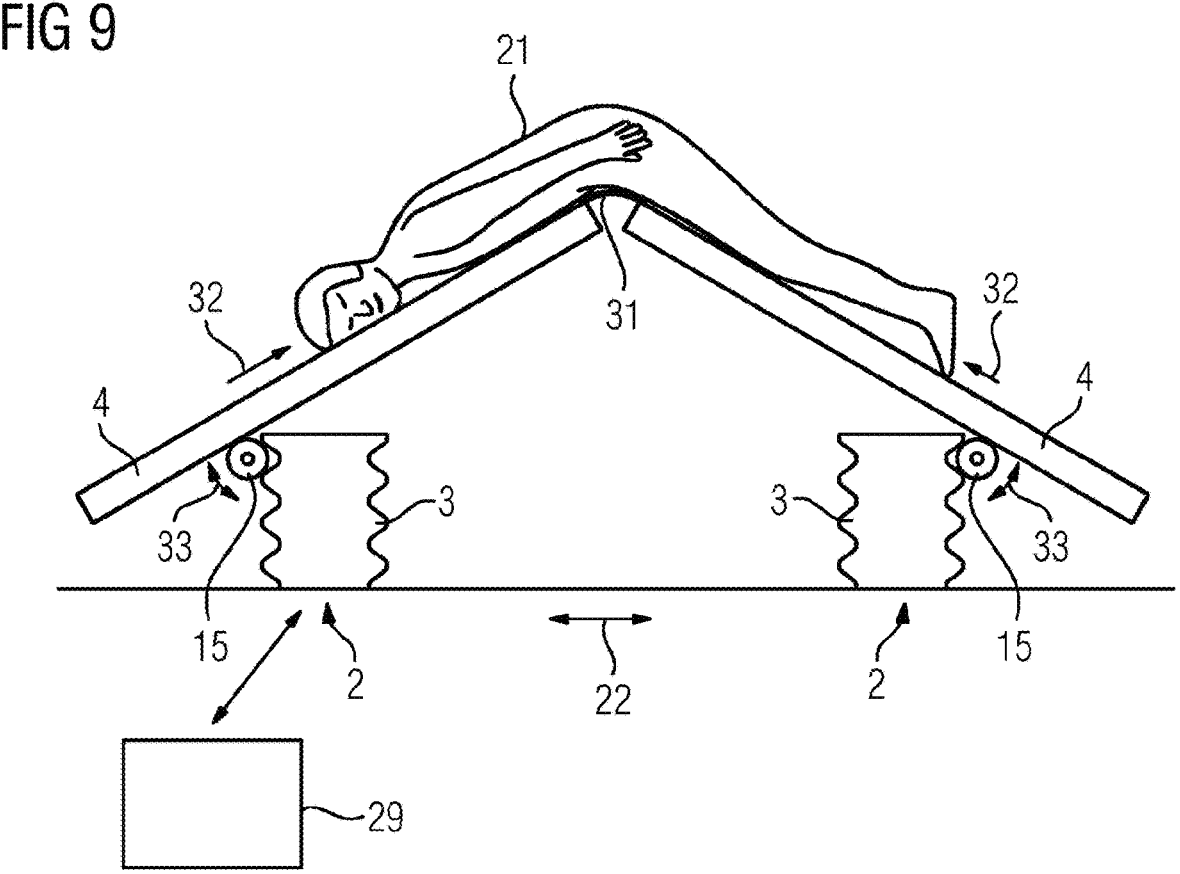
FIG. 9 depicts a schematic diagram of an embodiment in a second overall setting.

In FIG. 8, both partial boards 4 lie abutting each other in the same horizontal plane. The patient positioning device 28 may be used as a normal operating table here, in that the height adjustment devices and the longitudinal adjustment devices of the modules 2 are operated in a synchronized manner, meaning that the partial boards 4 move in the same way as a contiguous integral patient positioning board 5. Optional detachable connections 30 connect the partial boards 4 and may be detached if the partial boards 4 are to be pivoted by the pivot joints 15, as illustrated in FIG. 9.

There, the detachable connections 30 that function as a coupling are replaced by a flexible stretchable connection 31. The pivot joints 15 are triggered by the control device 29 in order to pivot each of the partial boards 4 upwards in the middle; the control device 29 simultaneously compensates for the separation caused by the pivoting (arrow 33) by longitudinal displacement as per the arrow 32. It is therefore possible, as in the case of operating tables according to the Jackson principle, to achieve an ideal position of the patient 21 for spinal interventions, where excellent imaging in the central x-ray imaging region 22 is also provided.

Figure 10:
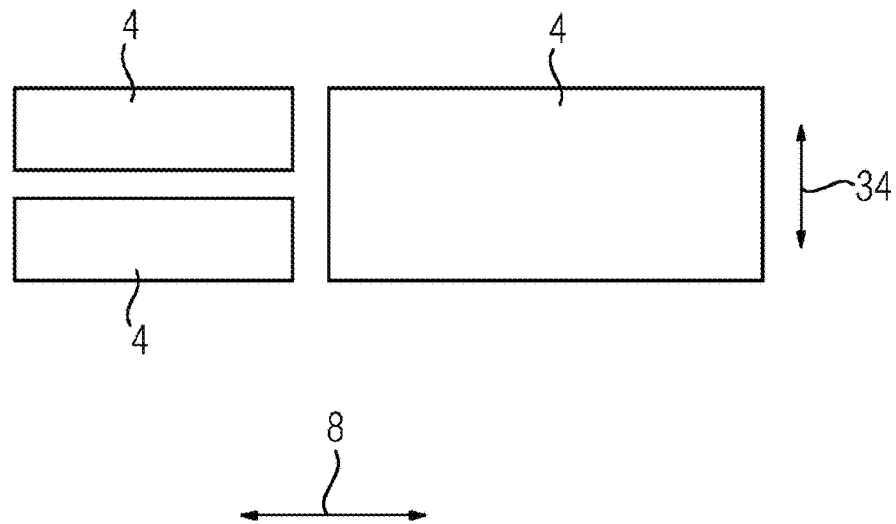
FIG. 10 depicts a view of an embodiment of the patient positioning device.
Figure 11:
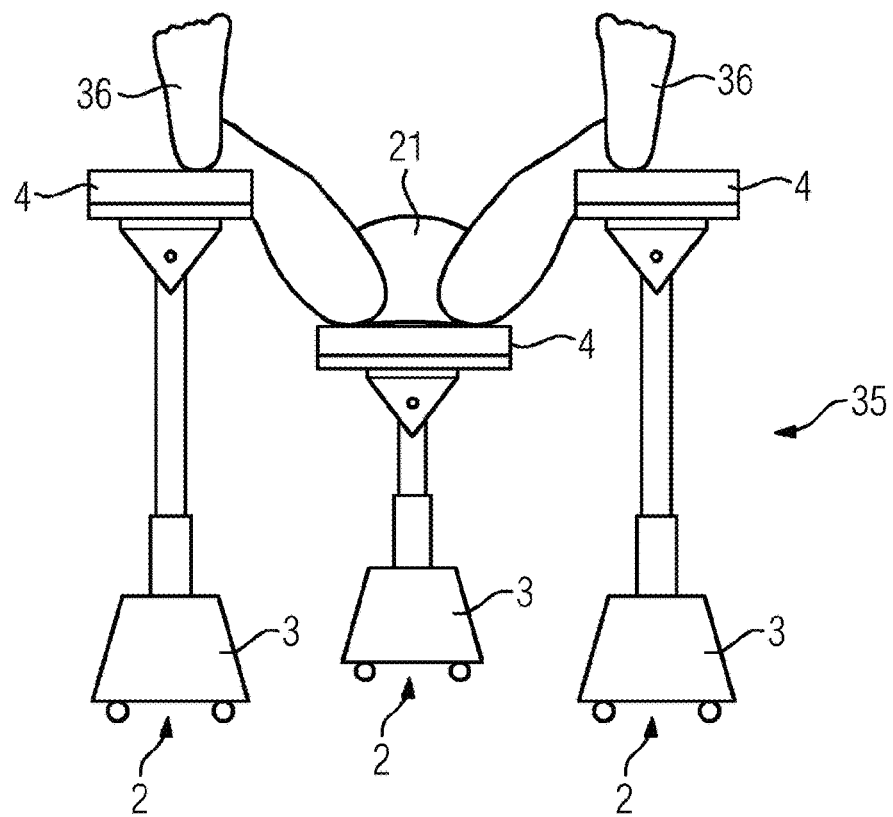
FIG. 11 depicts a view of an embodiment from the foot end.

FIG. 10 depicts a view of a further, fourth embodiment of a patient positioning device 35, including three partial boards 4, two of the partial boards 4, each of which is provided for a leg, being however adjacently disposed in a transverse direction 34. FIG. 11 depicts a view of the patient positioning device 35 from the foot end, the legs 36 being visibly supported on the partial boards 4, that are arranged higher here, of the modules 2 that are adjacently disposed in a transverse direction 34, the torso of the patient 21 being supported on the module 2 that is adjacent in a longitudinal direction 8. It is visibly possible to achieve a lithotomy position.

In the case of the patient positioning device 35 according to the fourth embodiment, lateral pivoting may also be realized for at least those partial boards 4 assigned to the legs 36, for example, by a corresponding swivel joint.

Figure 12:
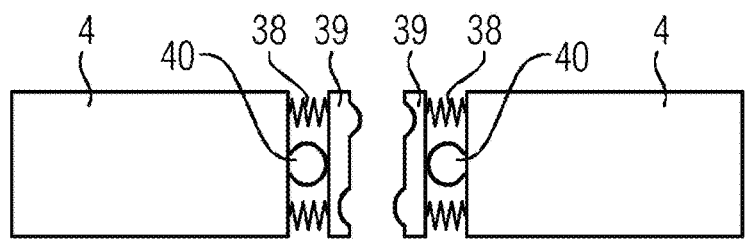
FIG. 12 depicts an embodiment of connections in a first state.
Figure 13:
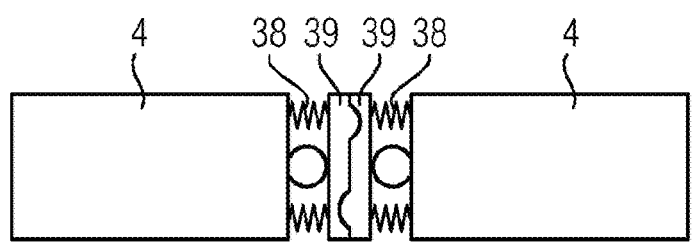
FIG. 13 depicts an embodiment of connections in a second state.
Figure 14:
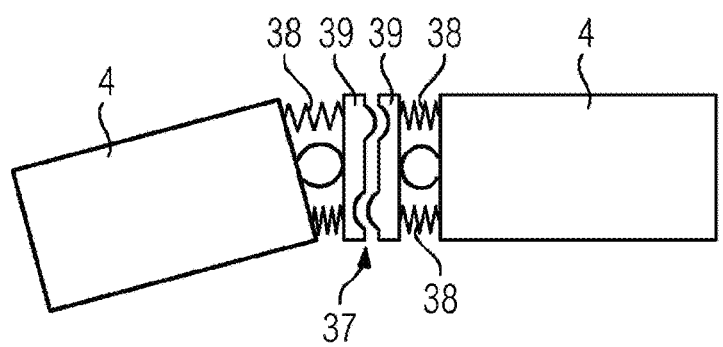
FIG. 14 depicts an embodiment of connections in a third state.

FIGS. 12 to 14 depict a possible realization for a connection 37 of two partial boards 4 that are adjacent in a longitudinal direction. A magnetic connector 39 in each case is visibly fastened via elastic fastener 38, springs in this case, to the respective facing surfaces of the partial boards 4. If the magnetic connectors 39 come close together as shown in FIG. 13, their surface profiling provides that they may only interconnect in a specific way because projections slip into corresponding recesses. FIG. 14 further illustrates how pivoting of the partial boards 4 relative to each other is absorbed by the elastic fastener 38 and is stabilized and guided by the articulated body 40, that is of cylindrical design here.

Figure 15:
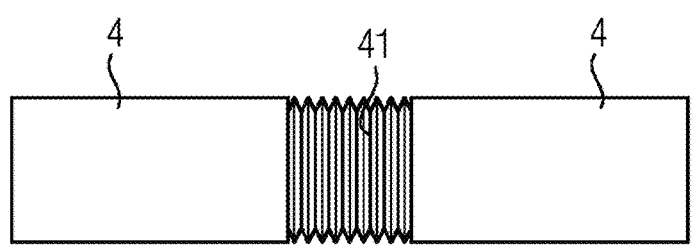
FIG. 15 depicts an embodiment of connections.

FIG. 15 depicts a further possibility for realizing a flexible and stretchable connection 41 between two partial boards 4 that are disposed adjacently in a longitudinal direction 8.

Connection is configured in the form of a bellows and capable of being pulled apart in a stretchable manner accordingly.

Figure 16:
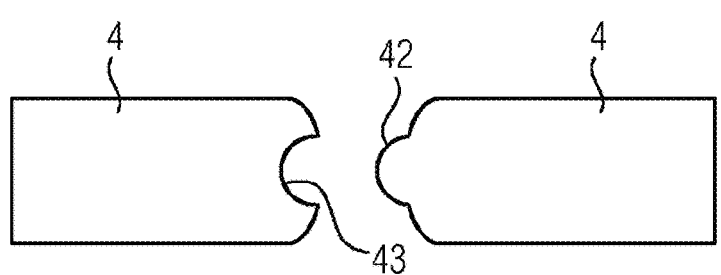
FIG. 16 depicts an embodiment of surfaces of adjacent partial boards.

FIG. 16 depicts a further possible possibility, in addition to connections, for reciprocal stabilization of partial boards 4 that are adjacent in a longitudinal direction 8, one of the corresponding surfaces having a guide projection 42 that may engage into a guide recess 43 of the facing surface of the other partial board 4. The guide projection 42 in this case includes a partially circular cross-sectional shape and is therefore configured for example overall as a partial cylinder in a transverse direction. Furthermore, space for tilting the partial boards 4 is provided in the edge regions.

Figure 17:
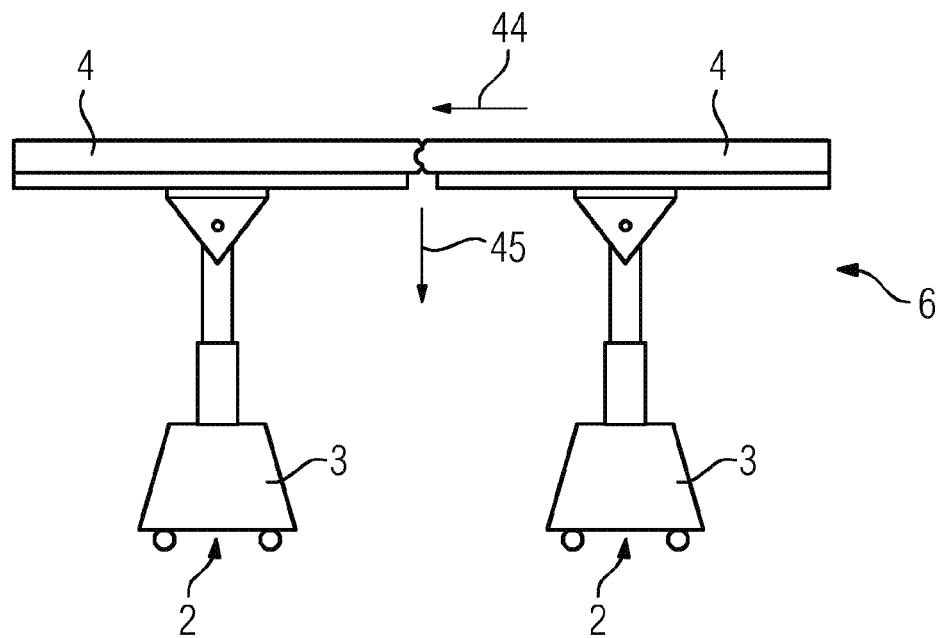
FIG. 17 depicts an illustration of the stabilization provided in FIG. 16.

FIG. 17 depicts how the engagement of the one partial board 4 into the other partial board 4 in accordance with the arrow 44 provides stability relative to gravity (arrow 45), based on the second embodiment.

Figure 18:
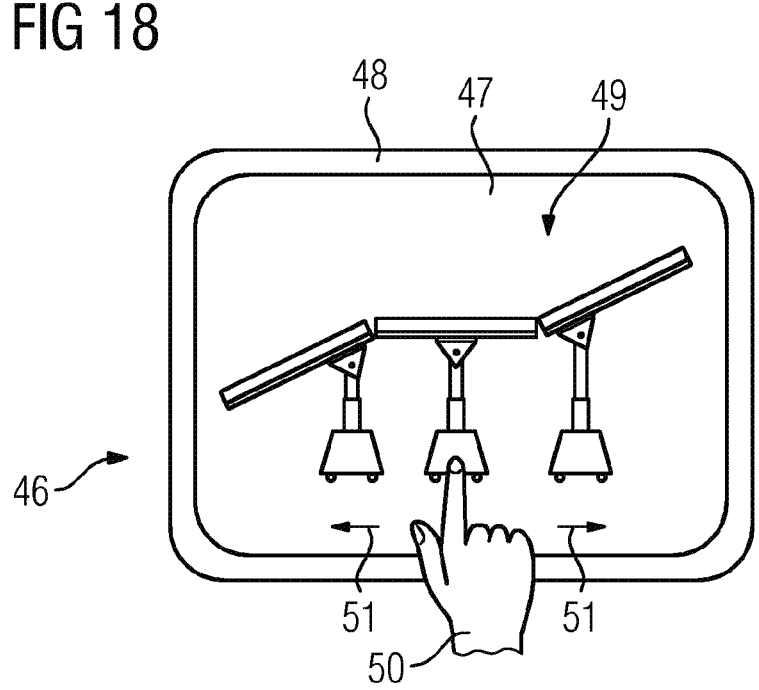
FIG. 18 depicts a first possible representation on a touch screen of an operating device according to an embodiment.

FIG. 18 depicts a possibility for operating the patient positioning device 1, 6, 28, 35 by an operating device 46 having a touch screen 47, for example a tablet 48. The tablet 48 may be connected to the control device 29 via a wireless communication connection.

A representation 49 of the patient positioning device 1 is shown in FIG. 18. Using the finger of their hand 50, a user may manipulate representational elements in order to effect corresponding settings at the patient positioning device 1. The carrier device 3 of the central module is selected here according to the arrows 51.

Figure 19:
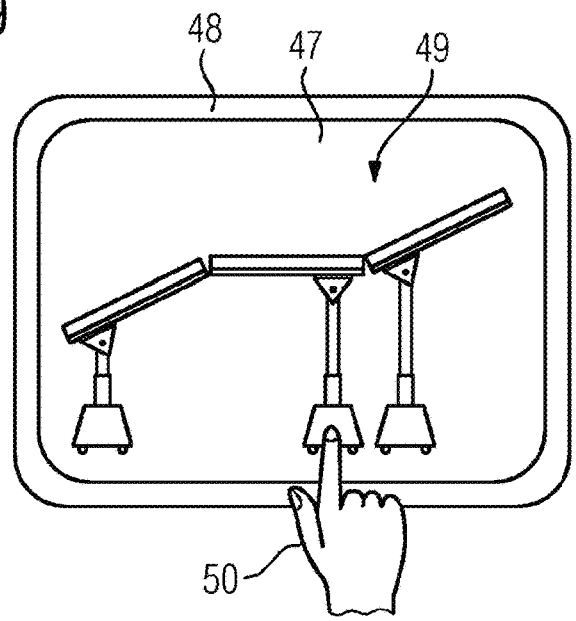
FIG. 19 depicts a second possible representation on the touch screen according to an embodiment.

FIG. 19 depicts the situation at a subsequent point in time where it may be seen that, by virtue of the actuators of the longitudinal adjustment device and the wheels 9, both carrier devices 3 are situated at the outside, such that a particularly large x-ray imaging region 22 is produced.

Figure 20:
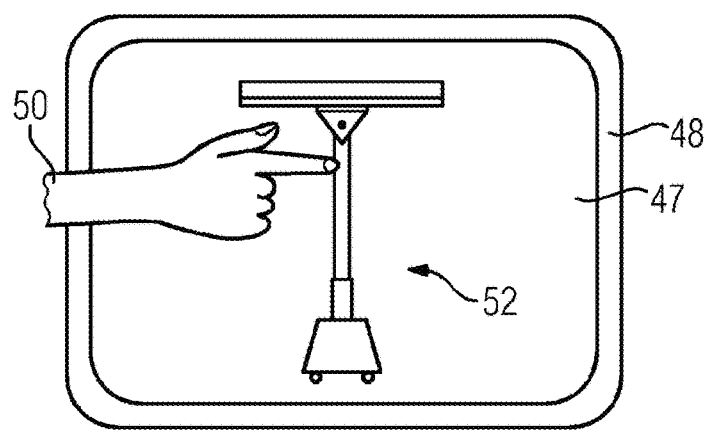
FIG. 20 depicts a third possible representation on the touch screen according to an embodiment.
Figure 21:
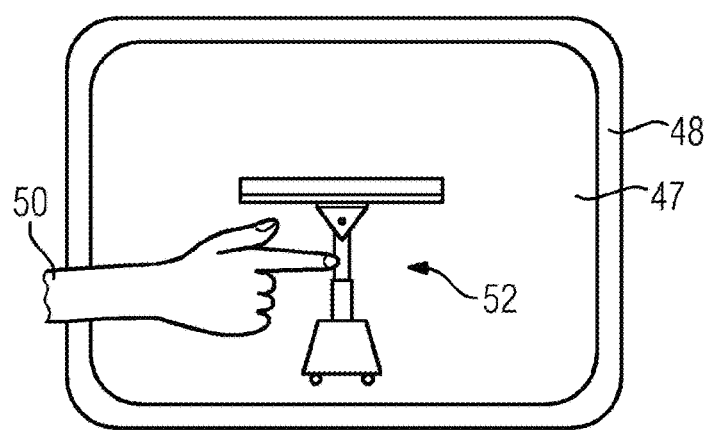
FIG. 21 depicts a fourth possible representation on the touch screen according to an embodiment.

FIGS. 20 and 21 show the operation of an individual module 2, of which a corresponding representation 52 is shown. The finger of the hand 50 manipulates the height adjustment device of the module 2, resulting in a corresponding height adjustment by the control device 29.

The operation depicts how the x-ray-transparency of the respective patient positioning device 1, 6, 28, 35 in the form of an operating table may be configured to the current requirements at any time, even intraoperatively, since (cf. for example also FIGS. 18 and 19) the actuators may be triggered in such a way that the positioning of the patient does not change but the relative position of the carrier devices 3 does. It is also shown in the embodiments that the modular operating table represented here offers x-ray transparency at points that may move, i.e., where the partial boards 4 meet each other, and where in the case of conventional operating tables, mechanical components and for example the pivot joint 15 are arranged.

While considerable mechanics are built into conventional implementations of adjustable operating tables, for example in order to realize an angle in the patient positioning board 5 and simultaneously to provide the stability of the angled operating table, the assembly of partial boards 4 proposed here, the partial boards 4 being mounted on carrier devices 3 that work synchronously at certain times and communicate via the control device 29, is able to provide a jointless patient positioning board 5 that may be angled such that the patient 21 is more easily accessible for the purpose of diagnostic imaging methods, x-ray imaging in this case.

It is to be understood that the elements and features recited in the appended claims may be combined in different ways to produce new claims that likewise fall within the scope of the present embodiments. Thus, whereas the dependent claims appended below depend from only a single independent or dependent claim, it is to be understood that these dependent claims may, alternatively, be made to depend in the alternative from any preceding or following claim, whether independent or dependent, and that such new combinations are to be understood as forming a part of the present specification.

While the present embodiments have been described above by reference to various embodiments, it may be understood that many changes and modifications may be made to the described embodiments. It is therefore intended that the foregoing description be regarded as illustrative rather than limiting, and that it be understood that all equivalents and/or combinations of embodiments are intended to be included in this description.

The invention claimed is:

1. A patient positioning device for an x-ray imaging device, the patient positioning device comprising:
at least two independent and flexible modules each comprising a carrier device and a partial board that when combined form an x-ray-transparent patient positioning board configured to position a patient in a longitudinal direction;
wherein each respective partial board is mounted on a respective carrier device, and
wherein each respective carrier device includes at least one pivot joint for pivoting the respective partial boards about a transverse axis that extends horizontally to the longitudinal direction.

2. The patient positioning device of claim 1, wherein each carrier device includes at least one height adjustment device configured for height adjustment of the respective partial board, at least one longitudinal adjustment device configured for longitudinal displacement of the respective partial board, or at least one height adjustment device and at least one longitudinal adjustment device.

3. The patient positioning device of claim 2, wherein each carrier device is configured such that at least one end position of the longitudinal adjustment a center of gravity remains above a footprint of the carrier device, a respective height adjustment device of each carrier device is configured as a telescopic device, or the longitudinal adjustment includes at least one guide rail.

4. The patient positioning device of claim 2, wherein each pivot joint, each adjustment device, or each pivot joint and each adjustment device is assigned a triggerable actuator for respective adjustment, wherein the patient positioning device further comprises a control device configured to trigger all actuators.

5. The patient positioning device of claim 4, wherein the control device is configured to compensate at least partially for a separation between the partial boards caused by pivoting of the partial boards by longitudinal displacement, height adjustment, or longitudinal displacement and height adjustment of the partial boards.

6. The patient positioning device of claim 4, wherein the control device is configured to receive signals from an operating device that is assigned to the patient positioning device, wherein basic arrangements assigned to different types of operation are stored in the control device and then implemented when a corresponding basic arrangement is selected by a user.

7. The patient positioning device of claim 6, wherein the operating device is a mobile device comprising a touch screen configured for displaying a manipulatable representation of the patient positioning device.

8. The patient positioning device of claim 4, wherein at least two of the partial boards abut each other in a plane-and the control device is configured to trigger the at least one height adjustment device and at least one longitudinal adjustment device to achieve overall movement of a complete patient positioning board.

9. The patient positioning device of claim 1, wherein the pivot joints are arranged at an outside in the longitudinal direction in or on the respective carrier device.

10. The patient positioning device of claim 1, wherein at least two adjacent partial boards are interconnected on respective facing surfaces of the at least two adjacent partial boards by a connection that is at least one of detachable, flexible, or stretchable.

11. The patient positioning device of claim 10, wherein for at least two of the at least two adjacent partial boards, at least one of the facing surfaces of the two adjacent partial boards or the connection includes at least one guide projection that engages into a corresponding guide recess of the other facing surface of the facing surfaces and allows an angular arrangement of the partial boards relative to each other when engaged.

12. The patient positioning device of claim 11, wherein the guide projection is partially spherical or partially cylindrical or at least one of the surfaces perpendicular to the longitudinal direction and to a transverse direction, and adjacent to the at least one guide projection or the corresponding guide recess, is configured to recede or allow room for the at least two partial boards to tilt relative to each other.

13. The patient positioning device of claim 1, wherein the patient positioning board is divided centrally into two partial boards.

14. The patient positioning device of claim 1, comprising at least three partial boards.

15. The patient positioning device of claim 1, wherein all or groups of the carrier devices are structurally identical.

16. The patient positioning device of claim 1, wherein the carrier devices are configured be at least partially mobile.

17. The patient positioning device of claim 7, wherein the operating device is a tablet.

18. The patient positioning device of claim 8, wherein at least two of the partial boards abut each other in a horizontal plane.

19. The patient positioning device of claim 1, wherein at least two partial boards that are assigned to a leg of the patient are adjacently disposed in a transverse direction.

20. The patient positioning device of claim 16, wherein the carrier devices include wheels.

* * * * *